United States Patent [19]

Starch

[11] 4,311,695

[45] Jan. 19, 1982

[54] PERSONAL-CARE EMULSIONS COMPRISING A SILOXANE-OXYALKYLENE COPOLYMER

[75] Inventor: Michael S. Starch, Midland, Mich.

[73] Assignee: Dow Corning Corporation, Midland, Mich.

[21] Appl. No.: 99,309

[22] Filed: Dec. 3, 1979

[51] Int. Cl.$^3$ .................... A61K 31/695; A61K 31/74
[52] U.S. Cl. ...................................... 424/184; 424/78
[58] Field of Search .......................................... 424/184

[56] References Cited

U.S. PATENT DOCUMENTS

| | | | |
|---|---|---|---|
| 3,489,690 | 1/1970 | Lachampt et al. | 252/308 |
| 4,057,622 | 11/1977 | Hase et al. | 424/78 |
| 4,122,029 | 10/1978 | Gee et al. | 252/309 |
| 4,151,304 | 4/1979 | Evans | 424/361 |

FOREIGN PATENT DOCUMENTS 1158139 10/1966 United Kingdom .
1221156 3/1971 United Kingdom .

*Primary Examiner*—Frank Cacciapaglia, Jr.
*Attorney, Agent, or Firm*—George A. Grindahl

[57] ABSTRACT

Water-in-oil type emulsions are disclosed wherein the water phase comprises a water-soluble alcohol and the oil phase comprises a volatile component and a soluble personal-care component.

The emulsions further comprise certain polydiorganosiloxane-polyoxyalkylene copolymers and, optionally, a silicon-free organic surfactant having an HLB value of from 2 to 10.

A preferred composition is a personal-care emulsion composition wherein the volatile, oil-phase component is a methylsiloxane fluid.

4 Claims, No Drawings

PERSONAL-CARE EMULSIONS COMPRISING A SILOXANE-OXYALKYLENE COPOLYMER

BACKGROUND OF THE INVENTION

This invention relates to personal-care emulsion compositions of the water-in-oil type comprising a copolymer of siloxane units and oxyalkylene units. More specifically this invention relates to dry-feeling, personal-care lotions and creams of said water-in-oil type wherein the oil phase comprises a volatile component and at least one personal-care component.

Water-in-oil type personal-care compositions which comprise a siloxane-oxyalkylene copolymer or a volatile oil-phase component are disclosed in U.K. Pat. Nos. 1,158,139 and 1,221,156 and are of some interest for this invention; however, the disclosure of Gee et al., U.S. Pat. No. 4,122,029 is pertinent background for this invention because it discloses personal-care compositions which comprise a siloxane-oxyalkylene copolymer and a volatile oil-phase component.

While the compositions of Gee et al. encompass desirable personal-care lotions and creams comprising oil-insoluble components they do not relate to compositions which comprise the oil-soluble components which are so widely used in personal-care products.

Water-in-oil type personal-care compositions comprising oil-soluble efficacious components are disclosed in U.S. Pat. Nos. 3,489,690; 4,057,622 and 4,151,304; however, these compositions lack the dry-feeling that is possessed by the compositions of the present invention.

SUMMARY OF THE INVENTION

It is an object of the present invention to provide personal-care emulsion compositions of the water-in-oil type wherein the oil phase comprises a volatile component and at least one non-silicone personal-care component dissolved therein. It is another object of this invention to provide personal-care emulsion compositions wherein said volatile component comprises a volatile silicone liquid.

It has now been found that dry-feeling personal-care compositions of the water-in-oil type can be prepared by including a water-soluble alcohol in the water phase and an oil-soluble personal care component in a volatile oil phase and employing a polydiorganosiloxane-polyoxyalkylene copolymer of Gee et al. as an emulsifier. Unexpectedly, auxiliary emulsifiers are not needed in the compositions of the present invention to provide emulsion stability.

DETAILED DESCRIPTION OF THE INVENTION

This invention relates to an emulsion composition consisting essentially of (a) 25 to 80 parts by weight of a water-alcohol solution, the weight ratio of water to alcohol in said solution being from 5/95 to 95/5, (b) 8 to 73.5 parts by weight of a volatile liquid having a normal boiling point of less than 250° C., said volatile liquid being selected from the group consisting of methylsiloxane fluids having the average unit formula $$(CH_3)_a SiO_{(4-a)/2}$$

wherein a has an average value of from 2 to 3 inclusive, paraffinic hydrocarbon fluids and their mixtures, (c) 1 to 10 parts by weight of a personal-care component which is soluble in said volatile liquid, and (d) 0.5 to 2 parts by weight of a polydiorganosilozane-polyoxyalkylene copolymer containing at least one polydiorganosiloxane segment consisting of $$R_b SiO_{(4-b)/2}$$

siloxane units wherein b has a value of from 0 to 3, inclusive, there being an average of approximately 2 R radicals per silicon in the copolymer, and R denotes a radical selected from the group consisting of methyl, ethyl, vinyl, phenyl and a divalent radical bonding a polyoxyalkylene segment to the polydiorganosiloxane segment, at least 95 percent of all R radicals being methyl; and at least one polyoxyalkylene segment having an average molecular weight of at least 1000 and consisting of from 0 to 50 mol percent polyoxypropylene units and from 50 to 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical; the weight ratio of polydiorganosiloxane segments to polyoxyalkylene segments in said copolymer having a value of from 2/1 to 8/1, the total of (a) plus (b) plus (c) plus (d) being 100 parts by weight.

Component (a) is an aqueous solution of at least one physiologically acceptable alcohol, such as ethanol isopropanol, propylene glycol or glycerol. Mixtures of alcohols can be used, if desired. The amount of alcohol that is present in component (a) may vary widely; ranging from as low as 5 percent to as much as 95 percent of component (a) on a weight basis. From an economic aspect component (a) should contain as little alcohol as possible; however, from a use aspect component (a) may contain more-than-minimum amounts of alcohol to control composition properties, such as viscosity and rheology.

The volatile liquid (b) is a fluid selected from the group consisting of methylsiloxane fluids, paraffinic hydrocarbon fluids and their mixtures, further detailed below. To be suitable as a volatile fluid in a personal-care composition component (b) should have a boiling point of less than 250° C. at atmospheric pressure. Methylsiloxane fluids and paraffinic hydrocarbon fluids meeting this parameter also typically have a viscosity at 25° C. of less than 10 millipascal-seconds (mPa·s). One millipascal-second equals one centipoise. To avoid an excessive cooling effect for the user of the compositions of this invention it is preferred that at least a portion of the volatile liquid have a normal boiling point of from 100° to 200° C.

The volatile methylsiloxane fluid (b) has the average unit formula $$(CH_3)_a SiO_{(4-a)/2}$$

where a has an average value of from 2 to 3 and consists of siloxane units selected from the group consisting of $(CH_3)_3SiO_{1/2}$, $(CH_3)_2SiO_{2/2}$, $CH_3SiO_{3/2}$ and $SiO_{4/2}$ units. Preferably the volatile methylsiloxane fluid consists essentially of dimethylsiloxane units and, optionally, trimethylsiloxane units. Of particular value as volatile liquid (b) are the cyclic siloxanes of the general formula $\{(CH_3)_2SiO\}_x$ and the linear siloxanes of the general formula $(CH_3)_3SiO\{(CH_3)_2SiO\}_y Si(CH_3)_3$, and their mixtures, wherein x is an integer of from 3 to 6 and y is an integer of from 0 to 4. A highly preferred methylsiloxane fluid is a mixture of said cyclic siloxanes wherein a major portion is composed of cyclic tetramer and/or cyclic pentamer. Preferably the volatile fluid (b) consists solely of one or more of said cyclic siloxanes.

Paraffinic hydrocarbon fluids suitable for use as component (b) in these compositions correspond to the average unit formula $C_nH_{2n+2}$ wherein n is an integer having a value of less than 15. A particularly suitable paraffinic hydrocarbon fluid is a high-purity isoparaffin, trademarked by and available from Exxon Corporation as Isopar ™. Gaseous paraffins are typically used under super-atmospheric pressure, such as in a pressurized dispenser, to keep them in the liquid state.

The volatile fluid, in addition to being a methylsiloxane fluid or a paraffinic hydrocarbon fluid, may be any mixture of said methylsiloxane fluid and said paraffinic fluid, such as a mixture of octamethylcyclotetrasiloxane and hexane or a mixture of decamethylcyclopentasiloxane and butane or a mixture of three or more of said cyclosiloxanes and paraffins. The emulsion compositions of this invention are stable to further dilution with a paraffinic hydrocarbon. This is of particular advantage in the preparation of personal-care emulsions which will not break when formulated in a pressurized dispenser using a gaseous paraffin, such as isobutane, as the propellant.

Methylsiloxane fluids and paraffinic hydrocarbons, suitable for use as volatile fluid (b) in the compositions of this invention, are well known in the chemical and polymer arts; many are commercially available.

Component (c) is any personal-care product, such as an emollient, a barrier agent, a grooming agent, a healing agent and a medicament which is soluble in the volatile liquid (b). Personal-care components include those that are intended for cosmetic purposes; such as for hair-grooming and skin-softening and/or for physiological purposes, such as for treating skin conditions, such as chapped skin, athlete's foot and dermatitis and for cleansing.

Examples of personal-care components that are useful in the compositions of this invention include, but are not limited to; ester waxes, oils and fats of animal or vegetable origin, such as spermaceti wax; beeswax, carnauba wax, lanolin wax, coconut oil, castor oil and lanolin oil; fatty alcohols such as cetyl alcohol, stearyl alcohol and lauryl alcohol; fatty acids acids such as stearic acid and palmitic acid; alkyl esters of fatty acids such as the methyl, ethyl or isopropyl ester of said fatty acid; hydrocarbon oils and waxes such as mineral oil, petrolatum, perhydrosqualene and paraffin wax.

Component (d) is a polydiorganosiloxane-polyoxyalkylene copolymer containing at least one polydiorganosiloxane segment and at least one polyoxyalkylene segment. The polyoxyalkylene segments may be bonded to the polydiorganosiloxane segments with silicon-oxygen-carbon bonds and/or with silicon carbon bonds. Although component (d) is not soluble in water and is therefore not subjected to vigorous hydrolysis in the compositions of this invention, it is preferred that the copolymer (d) have silicon-carbon bonding instead of the more hydrolyzable silicon-oxygen-carbon bonding joining the polyoxyalkylene segments to the polydiorganosiloxane segments.

The polydiorgnaosiloxane segments of the copolymer (d) consist of siloxane units which are interlinked by Si—O—Si linkages and which have the formula $$R_bSiO_{(4-b)/2}.$$

The value of b may range from 0 to 3 for said siloxane units with the provision that there is an average of approximately 2, i.e. from 1.9 to 2.1 R radicals for every silicon atom in the copolymer. Suitable siloxane units thus include $R_3SiO_{1/2}$, $R_2SiO_{2/2}$, $RSiO_{3/2}$, and $SiO_{4/2}$ siloxane units taken in such molar amounts so that b has an average value of approximately 2 in the copolymer. Said siloxane units may be arranged in linear, cyclic and/or branched fashion.

The R radicals of copolymer (d) may be any radical selected from the group consisting of methyl, ethyl, vinyl, phenyl, and a divalent radical bonding a polyoxyalkylene segment to the polydiorganosiloxane segment. At least 95 percent of all R radicals in the copolymer (d) are methyl radicals; preferably there is at least one methyl radical bonded to each silicon atom in (d). Divalent R radicals preferably contain no more than 6 carbon atoms. Examples of divalent R radicals include —O—, —$C_mH_{2m}O$—, —$C_mH_{2m}$— and —$C_mH_{2m}CO_2$— where m is an integer greater than zero.

Illustrative of the siloxane units that make up the polydiorganosiloxane segments of the copolymer (d) are the following, where Me denotes methyl and Q denotes said divalent R radical together with its bonded polyoxyalkylene segment: $R_3SiO_{1/2}$ units such as $Me_3SiO_{1/2}$, $Me_2(CH_2=CH)SiO_{1/2}$, $Me_2(C_6H_5)SiO_{1/2}$, $Me(C_6H_5)(CH_2=CH)SiO_{1/2}$, $Me_2(CH_3CH_2)SiO_{1/2}$, $Me_2QSiO_{1/2}$, $MeQ_2SiO_{1/2}$, $Q_3SiO_{1/2}$, $Q_2(CH_3CH_2)SiO_{1/2}$, and $Me(C_6H_5)(Q)SiO_{1/2}$; $R_2SiO_{2/2}$ units such as $Me_2SiO_{2/2}$, $Me(C_6H_5)SiO_{2/2}$, $Me(CH_2=CH)SiO_{2/2}$, $(C_6H_5)_2SiO_{2/2}$, $MeQSiO_{2/2}$, and $Q(C_6H_5)SiO_{2/2}$; $RSiO_{3/2}$ units such as $MeSiO_{3/2}$, $C_6H_5SiO_{3/2}$, $CH_2=CHSiO_{3/2}$, $CH_3CH_2SiO_{3/2}$ and $QSiO_{3/2}$; and $SiO_{4/2}$ units.

It is to be understood that copolymer (d) may comprise one or more of said polydiorganosiloxane segments. The number of and average molecular weight of the polydiorganosiloxane segments in the copolymer is related to the desired weight ratio, hereinafter described, of the polysiloxane and polyoxyalkylene segments in the polymer. Preferably copolymer (d) comprises one polydiorganosiloxane segment having bonded thereto one or more polyoxyalkylene segments.

The polyoxyalkylene segments of the copolymer (d) consist of oxyethylene units of the formula —$CH_2CH_2O$—, alone, or in combination with oxypropylene units of the formula —$CH_2CH(CH_3)O$—, an average of at least half of the oxyalkylene units in the polyoxyalkylene segments being oxyethylene units. Suitable emulsions of this invention are not formed when the polyoxyalkylene segments contain more than 50 mol percent of the relatively hydrophobic oxypropylene unit. The polyoxyalkylene segments thus correspond to the formula $\{-CH_2CH_2O-\}_p\{-CH_2CH(CH_3)O-\}_q$ wherein the oxyalkylene units may be arranged in any suitable fashion such as random, alternating and block. The average values of p and q are such that the value of p is equal to, or greater than, the value of q and the sum of p+q is sufficient to provide an average molecular weight of at least 1,000 for the polyoxyalkylene segments. Preferably the average molecular weight of the polyoxyalkylene segments has a value of from 1,500 to 5,000.

The polyoxyalkylene segments of the copolymer (d) are bonded to the polydiorganosiloxane segments of said copolymer by at least one terminal portion of said polyoxyalkylene segment, said bonding being by way of a divalent R radical, hereinbefore described. It is to be understood that said bonding may be by both terminal portions of said polyoxyalkylene segment in those copolymers comprising more than one polydiorganosiloxane segments. Any terminal portion of the polyoxyalkylene segment of copolymer (d) that is not bonded to a polydiorganosiloxane segment is satisfied by a terminating radical. The type of said terminating radical is not critical and may be monovalent, thereby terminating one polyoxyalkylene segment, or polyvalent, thereby terminating more than one polyoxyalkylene segment. Said terminating radicals are made up of atoms selected from the group consisting of carbon, hydrogen, nitrogen and oxygen. Illustrative of said terminating radicals are hydrogen; hydroxyl, alkyl, such as methyl, ethyl, propyl, butyl, benzyl, aryl, such as phenyl; alkoxy such as methoxy, ethoxy, propoxy, butoxy, benzyloxy; aryloxy, such as phenoxy; alkenyloxy, such as vinyloxy and allyloxy; acyloxy, such as acetoxy, acryloxy and propionoxy and amino such as dimethylamino.

The number of and average molecular weights of the segments in the copolymer (d) are such that the weight ratio of polydiorganosiloxane segments to polyoxyalkylene segments in copolymer (d) has a value of from 2/1 to 8/1, and preferably from 2.5/1 to 4.0/1. This weight ratio will insure that the copolymer (d) has a preferential solubility in the volatile liquid, a condition necessary for the formation of stable water-in-oil type emulsions of this invention.

The weight ratio of polydiorganosiloxane segments to polyoxyalkylene segments in copolymer (d) is calculated on the basis of the total weight of polydiorganosiloxane and the total weight of polyoxyalkylene that is joined in the copolymerization process. For example, if 100 parts by weight of polydiorganosiloxane is joined completely by an addition process which does not produce a by-product, such as a reaction which utilizes the addition of silicon-bonded hydrogen radicals to ethylenic unsaturation, with 20 parts by weight of an unsaturated polyoxyalkylene, said weight ratio of the resulting copolymer has a value of 5. Of course, if said complete joining is accomplished by a displacement reaction which produces a by-product, the weight ratio of polydiorganosiloxane to polyoxyalkylene in the resulting copolymer will not be identical with the weight ratio of the corresponding reactants, due to the loss of the weight of the displaced groups. The error introduced into the calculation of said weight ratio by ignoring the loss of said displaced groups is usually insignificant. That is to say, the weight ratio of polydiorganosiloxane to polyoxyalkylene in copolymer (d) may be calculated from the weight of reactants that react to form the copolymer or said weight ratio may be determined by suitable analysis of the resulting copolymer itself. Suitable analytical techniques such as elemental analysis, nuclear magnetic resonance spectroscopy, silicon substituent analysis and infra-red spectroscopy may be found in "Analysis of Silicones", A. Lee Smith, Ed., John Wiley and Sons, New York, 1974.

Herein, copolymer means either a block arrangement of segments such as denoted by the formulae $(AB)_c$, $A(BA)_c$ and $B(AB)_c$ or a pendant arrangement of segments such as $(AB_d)_c$ or combinations thereof wherein A denotes a polydiorganosiloxane segment, B denotes a polyoxyalkylene segment and c and d denote integers greater than zero and greater than one, respectively.

Copolymers (d) may be prepared by modifications of the well-known methods described in the polydiorganosiloxane-polyoxyalkylene copolymer art. The following patents are hereby incorporated herein by reference to show the preparation of polydiorganosiloxane-polyoxyalkylene copolymers: Haluska, U.S. Pat. No. 2,868,824; Haluska, U.S. Pat. No. Re. 25,727; Bailey, U.S. Pat. No. 3,172,899; Pater, U.S. Pat. No. 3,234,252, Simmler, et al. U.S. Pat. No. 3,174,987; Bailey, et al., U.S. Pat. Nos. 3,562,786, 3,600,418 and 3,629,308; Holdstock, U.S. Pat. No. 3,629,165; and Gee et al., U.S. Pat. No. 4,122,029.

It is to be understood that the silicon-bonded reaction groups such as silicon-bonded hydrogen for addition reactions or silicon-bonded hydrolyzable radicals for displacement reactions are preferably completely reacted in the copolymer preparation process, but that trace amounts of said reaction groups may escape reaction with the polyoxyalkylene and may be found in the copolymer (d).

Non-essential components which are common to personal-care compositions of the art, such as perfumes, humectants, preservatives, colorants and electrolytes may be incorporated into the compositions of this invention provided they do not destablize the emulsion so as to cause a breaking or an inverting of the emulsion.

To confer additional stability to the emulsions of this invention one can optionally mix therewith one or more auxiliary surfactants in the manner described by Gee at al. in U.S. Pat. No. 4,122,029 and, optionally, from 0.1 to 2.0 percent by weight of an inorganic salt in the aqueous phase.

The auxiliary surfactant may be any silicon-free organic surfactant suitable for preparing emulsions of the water-in-oil type and having an HLB (hydrophilic-lipophilic balance) value of from 2 to 10 inclusive. Said surfactant may be anionic, cationic or non-ionic with respect to its hydrophilic portion. Examples of suitable surfactants include sodium capryl lactylate and sodium stearoyl lactylate as anionic surfactants, quaternary ammonium chlorides manufactured by Tomah Products, Inc. as Emulsifier Three TM and Emulsifier Four TM as cationic surfactants and polyethylene glycol (200) monolaurate, glycerol monolaurate, N,N-dimethylcaproamide, diethylene glycol monolaurate, sorbitan monolaurate and nonylphenoxy polyethoxyethanol as non-ionic surfactants. Other examples of suitable organic surfactants having an HLB value of from 2 to 10 may be found by reference to standard publications such as McCutcheon's, *Detergents and Emulsifiers*, Allured Publishing company, Ridgewood, N. J. 1974.

Component (a), the water-alcohol solution, accounts for from 25 to 80 parts by weight, based on 100 parts by weight of the total of components (a) through (d). From an economic consideration it is preferred that a maximum amount of component (a) be used without losing emulsion stability. Based on other considerations, such as emulsion rheology, it may be desirable to use a less-than-maximum amount of component (a). Generally, the compositions of this invention vary from mobile fluids to viscous lotions to gels as the proportion of the water-alcohol solution is increased and the proportion of polydiorganosiloxane-polyoxyalkylene copolymer is held constant in the composition.

Component (b), the volatile liquid, accounts for from 8 to 73.5, and preferably 10 to 30, parts by weight, based on 100 parts by weight of the components (a) through (d).

Component (c), the personal-care component, accounts for from 1 to 10 parts by weight, based on 100 parts by weight of the total of components (a) through (d), its upper limit being further restricted in some cases by its solubility in the volatile liquid (b) and/or the amount of said volatile liquid that is present in the composition.

Component (d), the siloxane-oxyalkylene copolymer, accounts for from 0.5 to 2 parts by weight, based on 100 parts by weight of the total of components (a) through (d). Preferably as little copolymer (d) is used as is necessary to form a stable emulsion of this invention. Generally, the compositions of this invention vary from mobile fluids to viscous lotions to gels as the proportion of copolymer (d) is increased and the proportion of water-alcohol solution is held constant in the composition.

A highly preferred composition of this invention consists of 70±1 parts of water, 5±1 parts of ethanol, 18±1 parts of volatile cyclopolydimethylsiloxane, 6±3 parts of personal-care component and approximately 1 part of a siloxane-oxyalkylene copolymer prepared as follows.

Polydiorganosiloxane-polyoxyalkylene Copolymer—The polydiorganosiloxane-polyoxyalkylene copolymer that was used in the following examples, and is a preferred siloxane-oxyalkylene copolymer, was prepared from a trimethylsiloxane-endblocked polydimethylsiloxane having a molecular weight of approximately 30,000 and having an average of approximately 4 of its dimethylsiloxane units replaced with methylhydrogensiloxane units, and a random equimolar polyglycol copolymer of ethylene oxide and propylene oxide having an average molecular weight of approximately 2550 and having allyloxy endgroups on one end and acetoxy endgroups on the other end. Two hundred twenty grams of the siloxane, 80.76 grams of the polyglycol and 75.19 grams of isopropanol were mixed and heated to reflux under dry nitrogen in a flask and the resulting solution was catalyzed with 0.15 ml. of a 1 molar solution of $H_2PtCl_6$ in isopropanol. The reaction mixture was heated at reflux for one hour and then devolatilized at 110° C. and 1.33 kilopascals (10 mm of Hg) pressure. The polydimethylsiloxane-polyoxyalkylene copolymer product had a siloxane/oxyalkylene weight ratio of approximately 2.7/1 and $-CH_2CH_2CH_2O-$ divalent radicals bonding the polyoxyalkylene portion to the polydimethylsiloxane portion by way of a silicon-carbon bond.

At the present time the best-known method for preparing the compositions of this invention is illustrated by the following examples wherein a warm aqueous phase comprising the water, the alcohol and any optionally added, non-essential components that are soluble therein, is added slowly, and in increments interrupted by periods of mixing, to a well-stirred, warm oil-phase comprising the volatile liquid, the personal-care component, the siloxane-oxyalkylene copolymer and any optionally added, non-essential components that are soluble therein. Other methods of emulsion preparation which provide stable water-in-oil emulsions are suitable, but care must be taken to prevent inversion of the emulsion to an oil-in-water emulsion during its preparation.

Now in order that those skilled in the art may better understand how the present invention can be practiced, the following examples are disclosed for purposes of illustrating and not limiting the invention. All percentages and parts are by weight unless otherwise stated.

EXAMPLE 1

A first mixture was prepared by mixing seventy parts of water and 5 parts of an alcohol/water (5/95 v/v) mixture and heating the solution to approximately 60° C. In another vessel a second mixture was prepared by mixing 5 parts of lanolin, 10 parts of decamethylcyclopentasiloxane and 10 parts of a mixture containing 2 percent water, 11 percent of the above-described polydimethylsiloxane-polyoxyalkylene copolymer and 87 percent of octamethylcyclotetrasiloxane at a sufficiently high temperature to melt the lanolin. The first warm mixture was slowly added, in 7 portions, to the second warm mixture under high shear using a homogenizer-mixer. Thorough mixing of the resulting emulsion was done after each addition, the last mixing being conducted for 5 minutes.

The resulting pourable skin-care lotion consisted of 70.6 percent water, 4.6 percent ethanol, 5 percent lanolin, 18.7 percent volatile silicone fluid and 1.1 percent siloxane-oxyalkylene copolymer. When applied to the skin the lotion feels dry and, after a short period of evaporation, leaves a layer of lanolin and siloxane-oxyalkylene copolymer on the skin.

EXAMPLE 2

A lotion was prepared according to Example 1 except that 5 parts of petrolatum was used instead of 5 parts of lanolin.

EXAMPLE 3

A lotion was prepared according to Example 1 except that 5 parts of mineral oil was used instead of 5 parts of lanolin. In this case additional heating was not needed when preparing the oil phase because the mineral oil was not a solid.

EXAMPLE 4

The preparation of Example 1 was repeated except that only 9.5 parts of the mixture of 2 percent water, 11 percent copolymer and 87 percent octamethylcyclotetrasiloxane was used and 0.5 parts of a non-ionic, polyethyleneglycol alkylether surfactant having an HLB value of 8 (Tergitol ® 15-S-3) was added. A shelf-stable skin lotion was obtained.

That which is claimed is:
1. An emulsion composition consisting essentially of
   (a) 25 to 80 parts by weight of a water-alcohol solution the weight ratio of water to alcohol in said solution being from 5/95 to 95/5,
   (b) 8 to 73.5 parts by weight of a volatile liquid having a normal boiling point of less than 250° C., said volatile liquid being selected from the group consisting of methylsiloxane fluids having the average unit formula

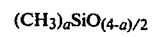

wherein a has an average value of from 2 to 3 inclusive, paraffinic hydrocarbon fluids and their mixtures,
   (c) 1 to 10 parts by weight of a personal-care component dissolved in said volatile liquid and selected from the group consisting of ester waxes, oils and fats of animal or vegetable origin, fatty alcohols, fatty acids, alkyl esters of fatty acids and hydrocarbon oils and waxes, and (d) 0.5 to 2 parts by weight of a polydiorganosiloxanepolyoxyalkylene copolymer containing at least one polydiorganosiloxane segment and at least one polyoxyalkylene segment, said polydiorganosiloxane segment consisting of $R_b SiO_{(4-b)/2}$ siloxane units wherein b has a value of from 0 to 3, inclusive, there being an average of approximately 2 R radicals per silicon atom in the copolymer, and R denotes a radical selected from the group consisting of methyl, ethyl, vinyl, phenyl and a divalent radical bonding a polyoxyalkylene segment to the polydiorganosiloxane segment, at least 95 percent of all R radicals being methyl; and said polyoxyalkylene segment having an average molecular weight of at least 1000 and consisting of from 0 to 50 mol percent polyoxypropylene units and from 50 to 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical; the weight ratio of polydiorganosiloxane segments to polyoxyalkylene segments in said copolymer having a value of from 2/1 to 8/1, the total of (a) plus (b) plus (c) plus (d) being 100 parts by weight.

2. The composition according to claim 1 wherein the volatile liquid (b) consists solely of cyclopolydimethylsiloxanes.

3. The composition according to claim 1 wherein the water-alcohol solution (a) consists of approximately 5 percent ethanol and 95 percent water.

4. The composition according to claims 1, 2 or 3 further containing an amount of at least one silicon-free organic surfactant having an HLB value of from 2 to 10 and being anionic, cationic or non-ionic with respect to its hydrophilic portion, said amount being a sufficient amount to provide additional stability to the emulsion.

* * * * *